United States Patent
Kanesaka et al.

[11] Patent Number: 5,954,707
[45] Date of Patent: Sep. 21, 1999

[54] CATHETER WITH LOCKING DEVICE

[75] Inventors: Nozomu Kanesaka; George A. Tashji, both of Hillsdale, N.J.

[73] Assignee: Uni-Cath Inc., Saddle Brook, N.J.

[21] Appl. No.: 09/094,642

[22] Filed: Jun. 15, 1998

[51] Int. Cl.⁶ ................................................. A61M 25/00
[52] U.S. Cl. .......................... 604/523; 604/264; 604/280
[58] Field of Search .................................. 604/264, 523, 604/533, 538, 539, 200

[56] References Cited

U.S. PATENT DOCUMENTS 5,352,198  10/1994  Goldenberg et al. ..................... 604/95
5,522,400   6/1996  Williams ................................. 120/772

*Primary Examiner*—Wynn Wood Coggins
*Assistant Examiner*—N. Kent Gring
*Attorney, Agent, or Firm*—Kanesaka & Takeuchi

[57] ABSTRACT

A catheter with a locking device is formed of a catheter and a locking device attached to a proximal end of the catheter. The locking device is formed of a cylindrical portion fixed to the proximal end of the catheter and having a dent at one side thereof, and a movable ring rotatably attached to the cylindrical portion and having a slit. The movable ring is rotatable to open and close the dent, so that when a portion of the catheter is placed in the dent through the slit, the movable ring is rotated to close the dent to securely hold the portion of the catheter in the slot. Accordingly, the catheter can be locked in the looped condition.

5 Claims, 2 Drawing Sheets

CATHETER WITH LOCKING DEVICE

BACKGROUND OF THE INVENTION AND RELATED ART STATEMENT

The present invention relates to a catheter with a locking device, more specifically, the catheter with the locking device which is integrally attached to the catheter to secure the catheter in a looped condition.

Catheters have been commonly used in various operations in the operating theater. According to the kind and object of the catheters, the catheters have various lengths. In some cases, the catheter has almost the same length as the height of the patient. If the catheter is relatively short, a manufactured catheter is retained in straight, but if the catheter is long, the catheter is looped and retained in hoop. In the straight or looped condition, the catheter is packed in a package.

Before use, a catheter has to be taken out from a package and prepared for use. In case a catheter is long, a catheter is looped or wound for easy handling and is left on top of a sterile cart. The catheter may be looped after use.

Although the catheter is looped or wound before or after use in the operating theater, there is no specific device for retaining the catheter in the looped condition. Therefore, the looped catheter may be accidentally unwound to cause a trouble.

In some catheters, a built-in hook is formed in a catheter hub. However, there is no specific method for locking the catheter in loop securely by the hook, so that there is always a chance to unwind itself inadvertently.

If the catheter is unwound and is dropped on a floor before it is used, the catheter may be contaminated. Thus, the catheter may not be used any more. After the catheter is used, since the catheter is put inside the patient's artery in many cases, the used catheter is ontaminated with patient's blood or body liquid and is very hazardous to the doctors and nurses. Thus, if the used catheter is unwind itself, it causes a trouble to doctors and nurses.

Accordingly, an object of the invention is to provide a catheter with a locking device, in which a catheter can be looped and locked into the locking device securely for easy handling.

Another object of the invention is to provide a catheter with a locking device as stated above, in which the catheter can be easily locked in a hoop condition and unlocked from the looped condition.

A further object of the invention is to provide a catheter with a locking device as stated above, in which the locking device can be applied to a regular catheter.

Further objects and advantages of the invention will be apparent from the following description of the invention.

SUMMARY OF THE INVENTION

To achieve the above objects, the present invention provides a catheter with a locking device, which is formed of a catheter having a distal end and a proximal end, and a locking device attached to the catheter. The locking device includes a cylindrical portion fixed to the proximal end of the catheter and having a dent at one side thereof, and a movable ring rotatably attached to the cylindrical portion. The movable ring includes a slit and is rotatable to open and close the dent, so that when a portion of the catheter is placed in the dent through the slit, the movable ring is rotated to close the dent to securely hold the portion of the catheter in the dent.

Accordingly, when the catheter is retained in the dent, the portion of the catheter is secured in the dent of the locking device. The catheter can be locked in the looped condition to form the catheter compact. The catheter may be used in the looped condition. If the catheter is to be straightened, the catheter in the looped condition is released by taking out the catheter from the dent through the slit.

In the catheter with the locking device of the invention, the locking device includes a grip extending from the cylindrical portion, and a hollow part is formed in the grip. The proximal end of the catheter is sealingly fixed to the hollow part of the shaft. Thus, for example, in the angioplasty procedure using the catheter, in case liquid or the like is required to be introduced into the catheter, liquid may be introduced into the hollow part of the shaft to deliver the liquid into the catheter.

The dent extends in an axial direction of the cylindrical portion, and has axial ends and a middle portion. The width of the dent at the middle portion is smaller than that at the axial ends thereof and gradually increases from the middle portion toward the axial ends. Thus, the friction between the dent and the catheter can be increased. Accordingly, the above structured dent can prevent the catheter from slipping or sliding inside the dent.

Further, the cylindrical portion includes at least one first annular dent and at least one stopping piece on an outer periphery thereof, and the movable ring includes at least one annular engaging piece and at least one second annular dent on an inner periphery thereof. The engaging piece engages the first dent in the cylindrical portion, and the stopping piece is situated in the second dent to thereby rotatably connect the cylindrical portion and the movable ring. Preferably, the cylindrical portion includes one stopping piece and two first annular dents on both sides of the stopping piece, and the movable ring includes two annular engaging pieces and one second annular dent between the two engaging pieces. Thus, the movable ring can rotate and engage the cylindrical portion without disengagement.

DETAILED DESCRIPTION OF PREFERRED EMBODIMENT

Hereunder, an embodiment of the invention will be explained with reference to the attached drawings.

Figure 1:
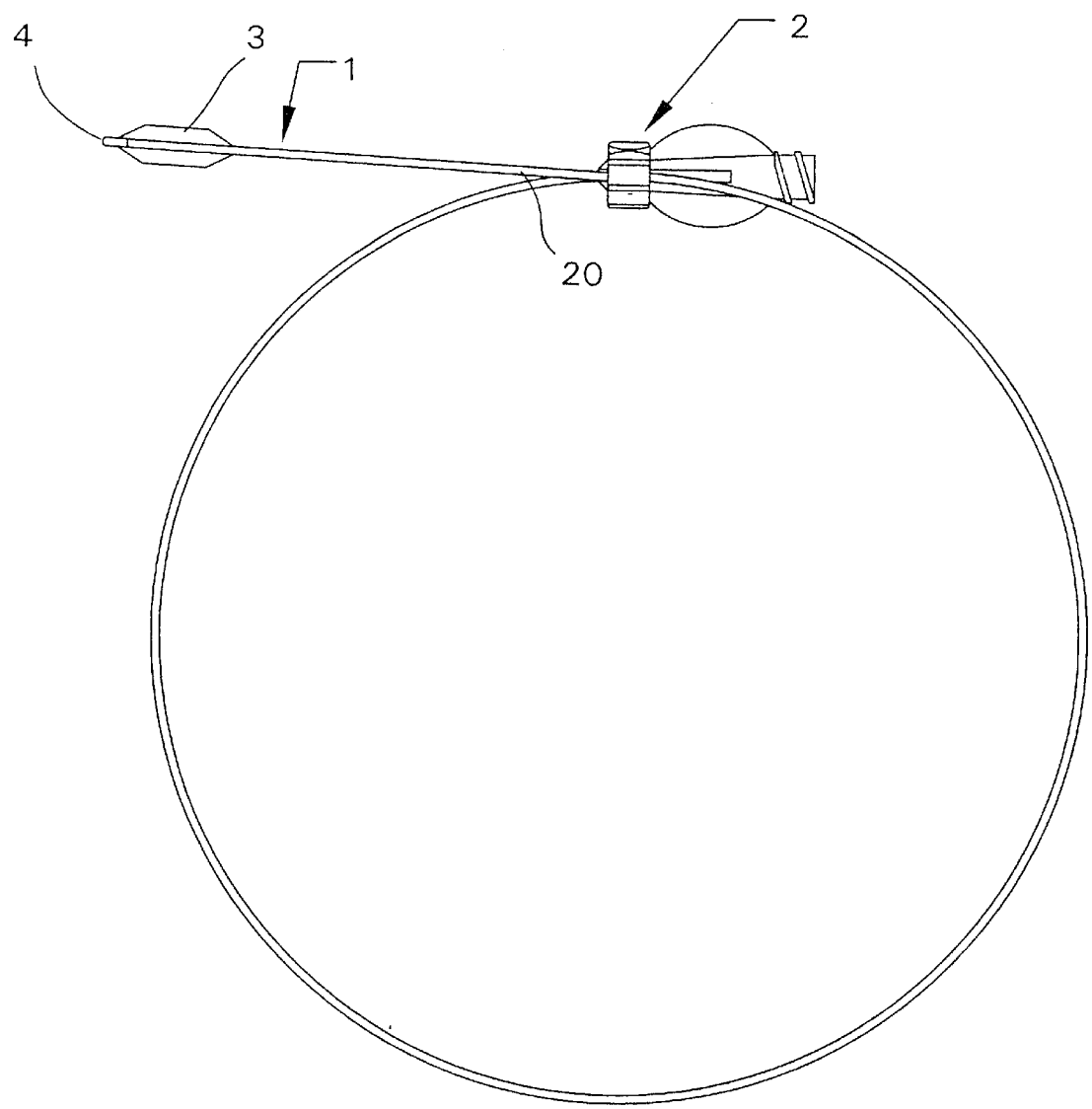
FIG. 1 is a schematic view of a catheter with a locking device according to an embodiment of the invention.

As shown in FIG. 1, a catheter with a locking device of the invention is formed of a lengthy catheter 1 and a locking device 2 attached to the catheter 1. The catheter 1 is an elongated lumen having a predetermined length, for example, about a half of a patient's height, and is provided with a balloon 3 at a distal end 4 thereof. The catheter 1 shown in FIG. 1 is looped into a hoop, and the locking device 2 secures the loop of the catheter 1.

Figure 2:
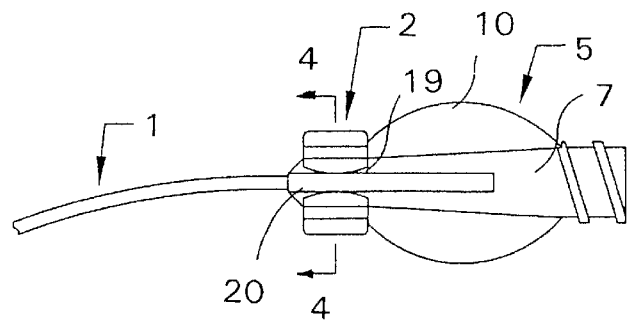
FIG. 2 is an enlarged view showing a proximal end part of the catheter with the locking device.
Figure 3:
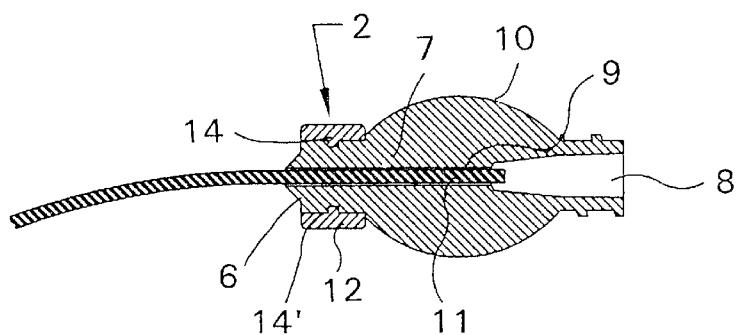
FIG. 3 is a vertical cross sectional view of FIG. 2.

FIGS. 2 and 3 show a detail of a proximal end part of the catheter with the locking device 2. As shown in FIG. 3, the locking device 2 is integrally formed with a handle 5, and includes a cylindrical portion 6 for constituting a part of the locking device 2. A center portion 7 for the handle 5 is integrally formed with the cylindrical portion 6 and extends rearwardly from the cylindrical portion 6. The center portion 7 includes a dent 8 at a rear center area thereof, and a through hole 9 extends through the cylindrical portion 6 and the center portion 7 to communicate with the dent 8. A grip 10 is also integrally formed with the center portion 7 and extends outwardly from the center portion 7.

A rear end portion 11 of the catheter 1 is inserted into the through hole 9, and sealingly attached to an inner wall of the cylindrical portion 6 and the center portion 7. Since the rear end portion 11 of the catheter 1 is sealingly attached to the center portion 7, for example, when the catheter with the locking device is used in the angioplasty procedure, liquid can be introduced into the dent 8 to provide the liquid into the catheter 1.

Figure 4:
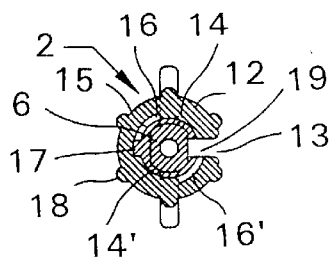
FIG. 4 is a cross sectional view taken along line 4—4 in FIG. 2.
Figure 5:
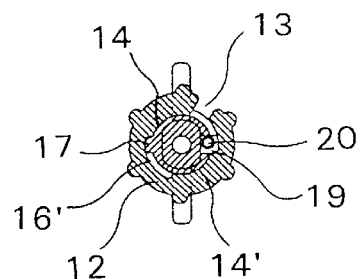
FIG. 5 is a cross sectional view showing the same section as in FIG. 4, wherein a slot shown in FIG. 4 is closed.

FIGS. 4 and 5 show the locking device 2 of the invention. A movable or rotational ring 12 is disposed around the cylindrical portion 6 and has a slit 13 at one portion. The movable ring 12 includes a pair of annular engaging pieces 14, 14' and an annular groove 15 between the engaging pieces 14, 14' on an inner surface thereof. Also, the cylindrical portion 6 includes two annular grooves 16, 16' and a stopper 17 between the grooves 16, 16' around the outer periphery thereof. The engaging pieces 14, 14' of the movable ring 12 are disposed in the annular grooves 16, 16' formed around the outer periphery of the cylindrical portion 6, and the stopper 17 of the cylindrical portion 6 is disposed in the groove 15 of the movable ring 12 to thereby permit the movable ring 12 to rotate in the predetermined rotational range.

The movable ring 12 has a plurality of projections 18 on the outer periphery thereof. The projections 18 help gripping the movable ring 12 when it is rotated.

As shown in FIGS. 2 and 4, the cylindrical portion 6 includes a dent 19 at one side, in which a part of the catheter 1 is to be disposed. The shape or width of the dent 19 seen from the side is the same as that of the slit 13. The width of the dent 19 is made small at the middle portion, and both ends of the dent 19 are gradually enlarged to have concave curves facing opposite to each other. Therefore, when the portion 20 of the looped catheter 1 is placed in the dent 19, the inner surfaces of the dent 19 contacting the portion 20 is increased to have sufficient friction between the portion 20 of the catheter 1 and the dent 19. Thus, this structure prevents the catheter from slipping in the dent 19.

In use, the slit 13 of the movable ring 12 is aligned with the dent 19, as shown in FIG. 4, into which the portion 14 of the catheter 1 formed in the hoop is inserted through the slit 13. Then, the movable ring 12 is rotated in the counterclockwise direction in FIG. 4, so that the dent 19 is closed by the wall of the movable ring 12 as shown in FIG. 5. In the condition shown in FIG. 4, the engaging piece 14' abuts against the stopper 17 to align the slit 13 with the dent 19, and in the condition shown in FIG. 5, the engaging piece 14 abuts against the stopper 17 to secure a closed condition.

Thus, by rotating the movable ring 12 around the cylindrical portion, the dent 19 can be opened and closed, and by inserting a portion of the looped catheter in the dent 19 and closing the dent 19 containing the portion of the catheter, the catheter can be secured in the looped condition.

According to the present invention, since the catheter is provided with the locking device at the proximal end thereof, when it is required to wind the catheter into a loop for shipping, preparation of the operation or after the operation, the catheter can be securely maintained in the looped condition by the locking device.

Also, according to the prevent invention, since the locking device is integrally formed with the catheter, other device or mechanism to secure the catheter in the looped condition are not required additionally.

While the invention has been explained with reference to the specific embodiments of the invention, the explanation is illustrative and the invention is limited only by the appended claims.

What is claimed is:

1. A catheter with a locking device, comprising:

a catheter having a distal end and a proximal end, and a locking device attached to the catheter, said locking device including a cylindrical portion fixed to the proximal end of the catheter and having a dent at one side thereof, and a movable ring rotatably attached to the cylindrical portion and having a slit, said movable ring being rotatable to open and close the dent so that when a portion of the catheter is placed in the dent through the slit, said movable ring is rotated to close the dent to securely hold the portion of the catheter in the slot.

2. A catheter with a locking device according to claim 1, wherein said dent extends in an axial direction of the cylindrical portion, and has axial ends and a middle portion, a width of the dent at the middle portion being smaller than that at the axial ends thereof and gradually increasing from the middle portion toward the axial ends.

3. A catheter with a locking device according to claim 1, wherein said cylindrical portion includes at least one first annular dent and at least one stopping piece on an outer periphery thereof, said movable ring including at least one annular engaging piece and at least one second annular dent on an inner periphery thereof, said at least one engaging piece engaging the at least one first dent in the cylindrical portion, and said at least one stopping piece being situated in the at least one second dent.

4. A catheter with a locking device according to claim 3, wherein said cylindrical portion includes one stopping piece and two first annular dents on both sides of the stopping piece, and said movable ring including two annular engaging pieces and one second annular dent between the two engaging pieces.

5. A catheter with a locking device according to claim 1, wherein said locking device includes a grip extending from the cylindrical portion, and a hollow part situated in the grip, said proximal end of the catheter being sealingly fixed to the hollow part of the grip.

* * * * *